United States Patent [19]

Glucksman

[11] Patent Number: 4,631,387
[45] Date of Patent: Dec. 23, 1986

[54] AROMA GENERATING APPARATUS WITH ELECTRICAL HEATING ELEMENT

[75] Inventor: Dov Z. Glucksman, Brookline, Mass.

[73] Assignee: Environmental Fragrance Technologies, Ltd., New York, N.Y.

[21] Appl. No.: 761,944

[22] Filed: Aug. 2, 1985

[51] Int. Cl.$^4$ .......................... H05B 3/20; A61L 9/03
[52] U.S. Cl. .................................... 219/272; 219/274; 219/275; 422/125
[58] Field of Search ............... 422/125, 126, 305, 306; 239/34, 51.5, 53, 54, 55-60, 128, 135, 136; 221/150 R, 150 A; 43/128, 129, 130, 125; 219/271-276, 501, 508, 510, 512, 515, 364

[56] References Cited

U.S. PATENT DOCUMENTS

| | | | |
|---|---|---|---|
| 658,793 | 10/1900 | Lockey | 422/124 |
| 1,403,548 | 1/1922 | Gudeman | 422/125 |
| 1,706,939 | 4/1929 | Rosenthal | 422/125 |
| 1,909,973 | 5/1933 | Lewis | 422/125 |
| 1,977,232 | 10/1934 | Ginder | 219/274 |
| 2,515,310 | 7/1950 | Messina, Jr. | 422/125 |
| 2,591,818 | 4/1952 | Huff | 422/125 |
| 2,611,068 | 10/1952 | Wellens | 219/272 |
| 2,618,892 | 11/1952 | Locks et al. | 446/268 |
| 2,690,500 | 9/1954 | Winberg | 219/272 |
| 2,741,003 | 4/1956 | David | 219/274 |
| 2,942,090 | 6/1960 | Diehl | 219/271 |
| 3,080,624 | 4/1963 | Weber, III | 354/6 |
| 3,119,650 | 1/1964 | Bilyeu | 422/125 |
| 3,180,999 | 4/1965 | Kuykendall | 219/501 |
| 3,247,358 | 4/1966 | Schmidt | 219/272 |
| 3,330,481 | 7/1967 | Dearling | 239/51.5 |
| 3,385,957 | 5/1968 | Munson | 219/501 |
| 3,431,393 | 4/1969 | Katsuda | 219/274 |
| 3,864,080 | 2/1975 | Valbona et al. | 422/4 |
| 3,895,928 | 7/1975 | Moran | 422/119 |
| 3,948,445 | 4/1976 | Andeweg | 239/53 |
| 3,972,473 | 8/1976 | Harrison | 239/34 |
| 4,084,732 | 4/1978 | Dearling | 222/402.17 |
| 4,085,309 | 4/1978 | Godel | 219/501 |
| 4,163,038 | 7/1979 | Nishimura | 422/305 |
| 4,327,278 | 4/1982 | Tomaro | 219/364 |
| 4,346,059 | 8/1982 | Spector | 422/125 |

FOREIGN PATENT DOCUMENTS

| | | | |
|---|---|---|---|
| 556003 | 4/1957 | Belgium | 219/271 |
| 0104758 | 4/1984 | European Pat. Off. | 422/305 |
| 2807383 | 2/1978 | Fed. Rep. of Germany | |
| 1443314 | 6/1973 | United Kingdom | |

OTHER PUBLICATIONS

Aroma Disc Player-Model FE200-Remington Products Inc. (Brochure) Use and Care Manual.

*Primary Examiner*—E. A. Goldberg
*Assistant Examiner*—Teresa J. Walberg
*Attorney, Agent, or Firm*—Lawrence S. Levinson; Robert E. Lee, Jr.

[57] ABSTRACT

An improved heater assembly for an aroma generating unit is disclosed. A serpentine heater element is disposed between mica insulating layers. The terminals of the heater element are extended through one of the layers. A two piece frame holds the heater element and insulating layers together. Both pieces have outer peripheral wall portions adapted for mating engagement when the frames are attached together. One of the pieces further comprises an inwardly divided flange while the other includes an inner peripheral wall portion which is shorter than the outer wall portion. When the heater assembly is joined together the insulating layers and intermediate heater element are held together between the flange and inner wall portion. A pair of opposite sides of the inner wall are spaced apart from the corresponding sides of the outer wall to form compartments which enclose the extended terminals of the heater element and the terminal ends of external power source leads such as an AC cord and related circuitry. The related circuitry includes a thermostat and rectifier circuit coupled in parallel between one pair of lead and heater terminals and a fuse coupled between the other pair.

18 Claims, 9 Drawing Figures

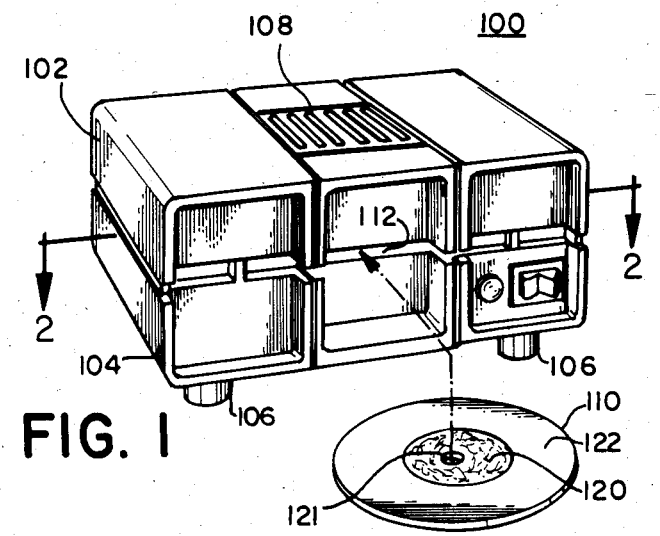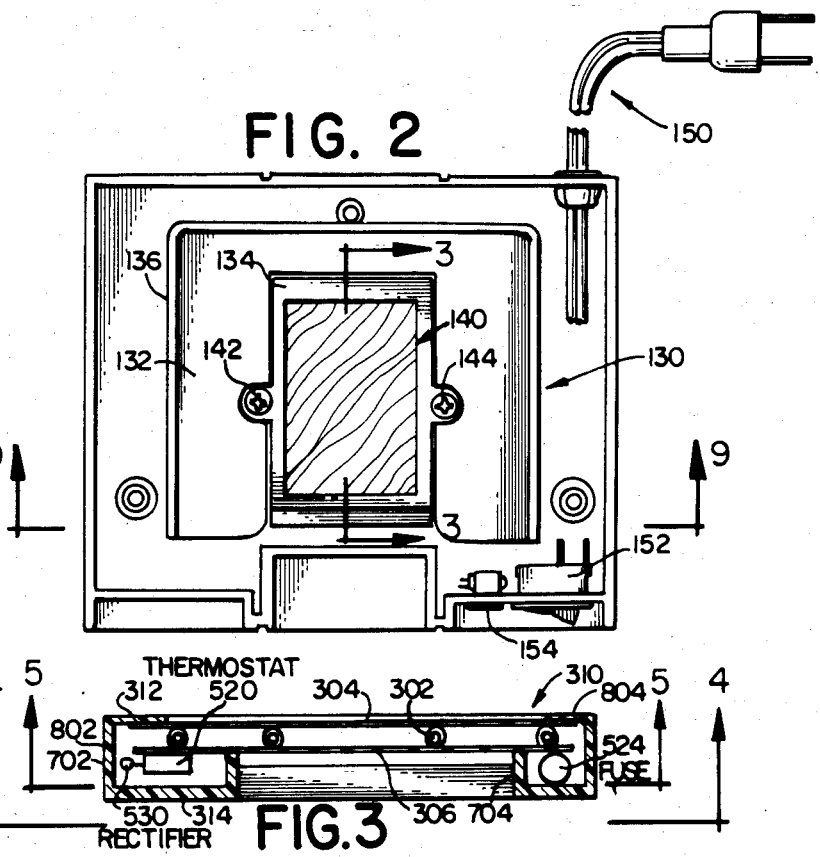

AROMA GENERATING APPARATUS WITH ELECTRICAL HEATING ELEMENT

BACKGROUND OF THE INVENTION

This invention relates to apparatus for producing an aroma in the surrounding atmosphere, and more particularly for doing so using an electrical heating element in proximity to a medium containing an aromatic liquid which element serves to create air currants that flow through the medium thereby assisting the evaporation of the aromatic liquid.

Many prior art devices exist wherein an electric light bulb in proximity to a liquid contained within a housing acts as the heating element to assist vaporization or evaporation of the liquid. See Gudeman U.S. Pat. No. 1,403,548; Rosenthal U.S. Pat. No. 1,706,939; Huff U.S. Pat. No. 2,591,818; Diehl U.S. Pat. No. 2,949,090; Weber III U.S. Pat. No. 3,080,624; and Spector U.S. Pat. No. 4,346,059. Other vaporizors are shown in Lockey U.S. Pat. No. 658,793 and Messina U.S. Pat. No. 2,515,310. Patents disclosing pressurized or mechanical dispensers of a liquid include Dearling U.S. Pat. No. 3,330,481; Valbona et al U.S. Pat. No. 3,864,080; Harrison U.S. Pat. No. 3,972,473; Dearling U.S. Pat. No. 4,084,732; and Hammond Br. Patent Spec. No. 1,443,314. Other documents of interest are the odor expelling toy in Locks et al U.S. Pat. No. 2,618,892; a lure for wild game which was a combustible fuel to generate heat in Bilyew U.S. Pat. No. 3,119,650; and German Pat. No. 2807383.

More recently aroma generating units which use an electrical heating element (other than a lamp) and disposable cartridge of some sort impregnated with the aromatic liquid to be dispersed have become popular. One such unit utilizes a flat circular cartridge adapted to be inserted horizontally into a slot within a housing. The unit contains a heating element below the slot.

The housing in the above described unit, except for the relatively narrow slot, completely encloses the heating element and associated electrical circuitry. Hence, there is little danger that in replacing cartridges one will come in contact with electrical parts or terminals. However, as designs change it becomes desirable to provide improved heating elements which will meet appropriate electrical safety requirements for use in more open housings where the heating element is more exposed during replacement of cartridges. At the same time heating element designs which provide automatic switching between more than one heat control setting and more uniform distribution of heat over the nearby disc are also desirable.

SUMMARY OF THE INVENTION

The present invention is directed to an improved electrical heating apparatus particularly for use in a replaceable cartridge aroma generating unit. A heating element is disposed between a pair of electrical insulating layers such as mica.

Access to the terminals of the heating element is provided by extending the terminals through at least one insulating layer. A frame is employed to clamp the insulating layers and heating element together along a perimeter region of the insulating layers. At the same time the frame in cooperation with an insulating layer forms a compartment surrounding the electrically extended heater element terminals.

In a preferred embodiment, a thermostat and a parallel rectifier circuit are coupled between one of the extended terminals and a terminal of an associated AC power source lead. The thermostat and rectifier circuits are disposed on an opposite side of the insulating layer from the heater element within a compartment formed by the frame and an insulating layer. A fuse is also included coupled between the other extended heater terminal and its associated lead terminal on the same side of the insulating layer as the termostat and rectifier circuits, also within a compartment formed by the frame and insulating layer.

In the preferred embodiment, the frame comprises two parts: a first section, such as the top, and a second section, such as the bottom. The top comprises a peripheral wall member and a flange extending inwardly therefrom to define a central open area. One of the insulating layers engages the flange.

The bottom comprises an outer peripheral wall portion adapted for mating engagement with the top wall portion, and an inner peripheral wall portion which is shorter than the outer wall portion and engages the other insulating layer. At least one side, and preferably two opposite sides, of the inner wall portion are spaced apart from corresponding sides of the outer wall portion. Together with the insulating layer the spaced apart sides form compartments for enclosing the heater element extended terminals and lead terminals and associated circuitry.

The above described heater element assembly is particularly suitable for aroma-generating units having a housing adapted for supporting a medium impregnated with aroma producing fluid and the heater element assembly in proximity thereto.

BRIEF DESCRIPTION OF THE DRAWINGS

FIG. 1 is a perspective view of an aroma generating unit adapted for receiving within a slot therein a replaceable cartridge;

FIG. 2 is a top view of a bottom portion of the unit of FIG. 1 taken along the lines and arrows 2—2 and including a preferred embodiment heater element assembly;

FIG. 3 is a cross sectional view of the heater element assembly of FIG. 2 taken along the lines and arrows 3—3;

DETAILED DESCRIPTION OF THE DRAWINGS

Figure 4:
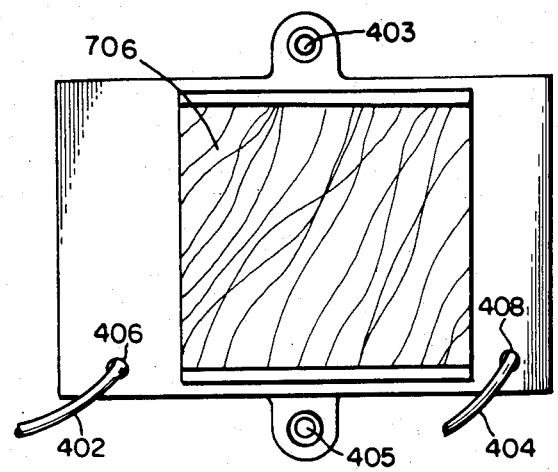
FIG. 4 is a bottom view taken along the lines and arrows 4—4 in FIG. 3 of the preferred embodiment heater assembly.

Referring now to FIGS. 1 and 2, a perspective view of an aroma generating unit designated generally 100 is shown. It is preferably made of molded plastic having a top 102 attached appropriately to the bottom 104. The bottom includes a plurality of feet 106 for resting the unit on a table top and spacing the bottom away therefrom. The bottom and top each includes a plurality of openings or air vents 108 in the top and 904 in the bottom.

The aroma generating unit 100 is adapted for receiving a disposable, relatively rigid circular cartridge 110 in front slot 112 formed between the top 102 and bottom 104. Cartridge 110 is impregnated, usually only in the center portion 120, with an aromatic liquid or oil. The remaining portion 122 of the cartridge 110 erves as a liquid or oil free portion for handling the cartridge for inserting or removing the cartridge into or from the unit 100. The center portion 120 of the cartridge also comprises perforation 121.

Figure 9:
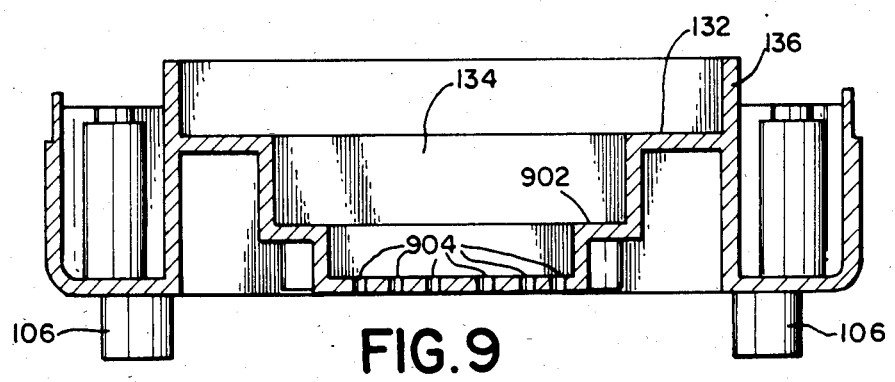
FIG. 9 is an enlarged cross sectional view or the bottom of the unit taken along the lines and arrows 9—9 in FIG. 2 with the heater assembly removed.

In FIG. 2, the bottom contains a tray designated generally 130 which comprises a platform area 132 with a central rectangular opening 134 and a surrounding upwardly extending wall 136. A heating means designated generally 140 is attached to the bottom 104 by screws 142 and 144 below the platform area 132 directly under the opening 134. When the cartridge is inserted into the slot, the portion 122 of the cartridge rests on the platform area 132 with center portion 120 positioned over the heating means 140. The wall 136 aids in properly positioning the cartridge 110 within the unit 100. FIG. 9 shows in cross section the platform area 132, opening 134, surrounding wall 136 and the level 902 at which the heater assembly 140 is positioned below the platform area 132 and the air vents 904.

The unit 100 comprises a two lead cord and plug designated generally 150 for coupling the unit 100 to a power source such as a 120 volt AC electrical socket. When the switch 152 is turned to the on position, power is applied to the heating means 140 and the red power on indication light 154 is turned on. As the heating means heats up the surrounding air an air current is created drawing air in from the bottom vents 904 past the center portion 120 of the cartridge, and out the top vents 108.

FIG. 3 is a cross sectional view of the heater assembly 140 taken along the lines and arrows 3—3 in FIG. 2. The heater assembly comprises a serpentine or rope heater element 302 positioned between planar, spaced apart and parallel mica insulating layers 304 and 306. The insulating layers 304 and 306 and element 302 are pressed or held together by a frame designated generally 310 comprising a top portion 312 and bottom portion 314, preferably made of high temperature plastic resin.

Figure 5:
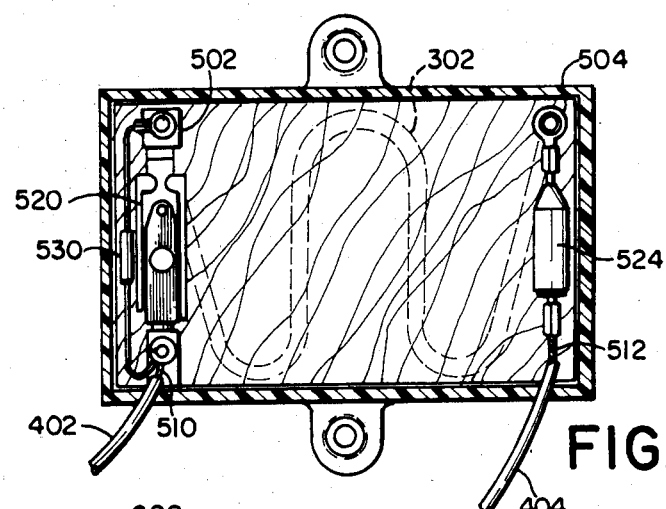
FIG. 5 is a bottom view taken along the lines and arrows 5—5 in FIG. 3 of the preferred embodiment heater assembly with the bottom portion of the frame removed.

FIG. 4 shows a bottom view of the assembly 140. Two insulated electrical leads 402 and 404 from cord and plug 150 pass through the bottom frame portion 314 at holes 406 and 408. Metal eyelets 403 and 405 hold frame portions 312 and 314 in compressive alignment. The holes in the eyelets are large enough to accommodate the shanks of screws 142 and 144. FIG. 5 is the same bottom view of the heater assembly 140 with the bottom frame portion 314 removed to expose the internal circuitry.

In FIG. 5, the heater element 302 comprises two terminals which are extended through insulating layer 306 by crimp connectors at 502 and 504 making the terminals electrically assessible from a side of the insulating layer opposite the heater element. Insulated leads 402 and 404 after they pass through bottom frame portion 304 have their ends stripped of insulation to expose electrical terminal ends 510 and 512.

In the preferred embodiment, a bimetallic thermostat 520 is coupled between the extended heater terminal at 502 and the exposed lead terminal 510 while a fuse 524 is coupled between the extended heater terminal at 504 and exposed lead terminal 512. When the air surrounding the thermostat 520 reaches a predetermined temperature thermostat 520 opens up to disconnect power to the heating element thereby controlling the temperature depending on the choice and setting of the thermostat 520. Fuse 524 protects the entire unit if for some reason the heater element should short circuit.

A more stable operating temperature is established by coupling a rectifier circuit 530 in parallel with thermostat 520 between the terminals at 502 and 510. When the bimetallic switch is closed there is no bias voltage applied across the diodes and they do not conduct. When the switch opens the diodes become conductive during one half the AC cycle and half wave rectification occurs thereby delivering only one half the power to the heating element that is delivered when the thermostat is closed. This reduces the range over which the temperature cycles during the opening and closing of the thermostat resulting in a more even distribution of the aroma within the ambient atmosphere with time.

Alternatively, the thermostat and rectifier circuit can be designed to produce an aroma burst cycle (thermostat closed) and an aroma maintenance cycle (thermostat open). In the preferred embodiment a bimetallic element is chosen which opens at approximately 90° C. and closes at approximately 60° C. When the unit is first turned on full power is applied and for approximately 3 minutes plus or minus ½ minute, the thermostat remains closed (burst made). The temperature at the cartridge center also rises to approximately 130° C. causing a high rate of volatization of the aromatic liquid. After 3 minutes, the thermostat opens and the power is delivered through the diode rectifier circuit 530 (maintenance mode). During this period the temperature of the cartridge center 120 stabilizes at just under 100° C. which still results in considerable volatization but not as much as in the burst mode. When the unit is turned off it cools off and the thermostat closes, ready for the next burst mode when the unit is turned on again.

Figure 6:
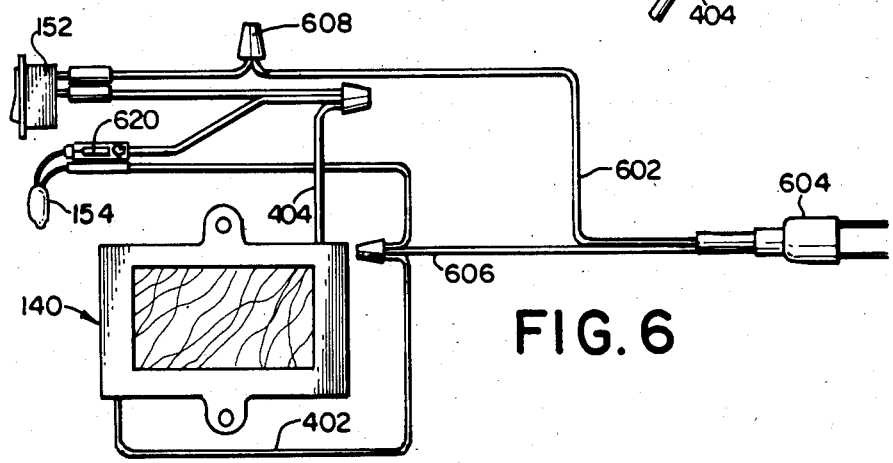
FIG. 6 is a lay out of the electrical circuit external to the electrical heater assembly shown connected thereto.

FIG. 6 is a layout of the electrical circuit of the unit 100 external to the heater assembly 140. One insulated lead 602 of plug 604 is coupled one side of switch 152 whose other side is coupled to one side of lamp 154 and to the heater assembly 140 as lead 404. The other side of the lamp 154 and lead 402 from the heater assembly 140 are coupled to the other insulating lead 606 of plug 604. Insulated wire nuts 608 are used throughout the electrical circuit.

A 33K resistor 620 is coupled in series with the neon lamp 154 to limit current flow through the lamp.

Figure 7:
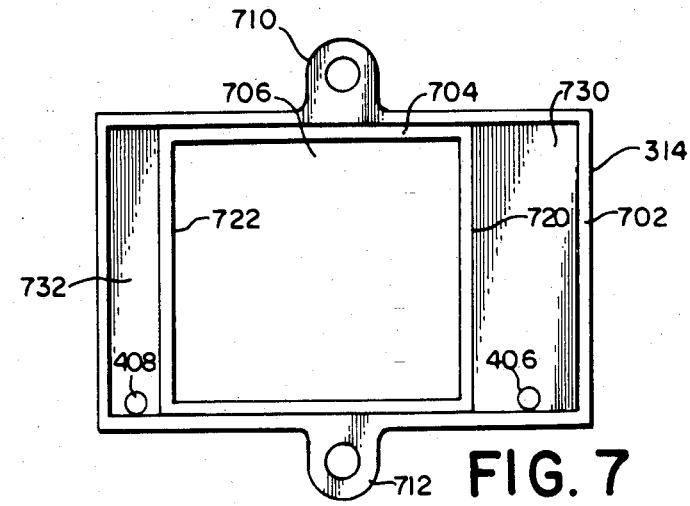
FIG. 7 is a top planar view of the bottom portion of the frame of the electrical heater assembly.
Figure 8:
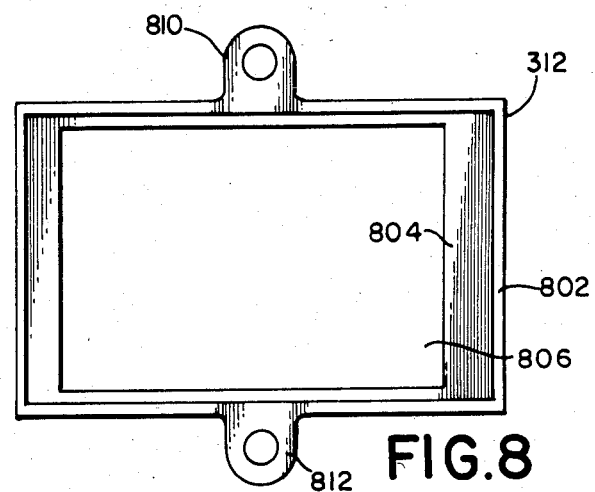
FIG. 8 is a bottom planar view of the top portion of the frame of the electrical heater assembly.

FIG. 7 is a top planar view of the bottom portion 314 of frame 310 while FIG. 8 is a bottom view of the top portion 312. The top planar portion 312 comprises an outer peripheral wall portion 802 and a peripheral flange 804 extending inwardly therefrom defining a central open area 806. The top portion further comprises a pair of tabs 810 and 812 opposite one another extending outwardly from opposite sides of the wall portion 802. The flange 804 is adapted to engage a peripheral portion of insulating layer 304 when the assembly is joined together.

The bottom portion 314 in FIG. 7 comprises an outer peripheral wall portion 702 adapted for mating engagement with the wall portion 802 when the top and bottom portions of the frame are joined together. The bottom portion further comprises an inner peripheral wall portion 704 which defines a center open area 706. The inner wall portion is shorter than the outer wall portion and is adapted to engage inulating layer 306 when the assembly is joined together. The bottom portion also comprises a pair of opposite tabs 710 and 712 which are adapted to align with tabs 810 and 812. All tabs comprise a center aperture or hole so that suitable attachment means can be employed to hold the frames together.

In the preferred embodiment, a pair of opposite sides 720 and 722 of the inner peripheral wall 704 are spaced apart from corresponding sides of the outer peripheral wall 702. The spaced apart walls together with the outer peripheral wall and insulating layer 306 form compartments 730 and 732 which completely surround any exposed electrical portions of the heater element and related circuitry and lead terminals.

This is more clearly shown in FIG. 3, which shows the engagement of the outer peripheral walls, the pressing together of the insulating layers and heating element between flange 804 and inner wall portion 704, and the containment of the fuse 524, rectifier circuit 530 and thermostat 520 by the compartments 730 and 732. Hence, the heating assembly is a self contained unit which can be used in closed aroma generating unit housings or more open ones where the heater assembly is more accessible when replacing aromatic liquid laden cartridges.

An additional feature of the improved heater assembly of the present invention is that the mica insulating layers are pressed into contact with the serpentine heater element which helps to distribute more evenly the heating effect of the heater assembly over a planar region. The frame is constructed so that it is open both below and above the bottom and top insulating layers, respectively, in the area of the heater element. Heated air currents rise in planar fashion entraining evaporated aromatic fluid for distribution into the atmosphere.

I claim:

1. An aroma generating apparatus comprising:
a housing with openings for allowing an air current to pass therethrough;
a medium impregnated with aroma producing fluid and removably supported by said housing at least partially within said air current; and
electrical heating means adapted for coupling to an external power source and supported by said housing proximate said medium when said medium is supported by said housing, said electrical heating means comprising:
a heating element disposed between substantially parallel and spaced apart electrical insulating layers, said heating element comprising at least a pair of terminals electrically extended through at least one of said insulating layers; and
a frame which clamps said insulating layers along a perimeter region thereof against said heating element and which cooperates with said at least one of said insulating layers to form a compartment surrounding said electrically extended terminals, said frame comprising:
first and second sections, said first section further comprising a peripheral wall member and a flange extending inwardly therefrom for engagement with the periphery of one of said insulating layers; and
said second section includes an outer peripheral wall member adapted for mating engagement with said first section peripheral wall member whose sides are shorter than said outer peripheral wall member, said inner peripheral wall member adapted to engage one of said insulating layers whereby said insulating layers and intermediate heating element are pressed together when said first and second sections are joined together, said inner peripheral wall member having at least one side spaced apart from an associated side of said outer wall member to form said compartment.

2. The apparatus of claim 1 wherein said electrical heating means further comprises:
a thermostat disposed within said compartment and coupled between one of said terminals and a terminal of an associated insulated power source lead passing through said frame.

3. The apparatus of claim 2 wherein said compartment also sourrounds said thermostat and said lead terminal.

4. The apparatus of claim 2 wherein said electrical heating means further comprises:
a rectifier circuit disposed within said compartment and coupled in parallel with said thermostat between said heater element terminal and said terminal of said associated lead.

5. The apparatus of claim 1 wherein a pair of opposite sides of said inner peripheral wall member are spaced apart from associated sides of said outer peripheral wall member to form a pair of compartments.

6. The apparatus of claim 5 wherein the flange of said first section and the inner peripheral wall of said second section define center planar areas of said insulating layers which are open to the surrounding atmosphere.

7. An electrical heating apparatus comprising:
a heating element disposed between substantially parallel and spaced apart electrical insulating layers, said heating element comprising at least a pair of terminals electrically extended through at least one of said insulating layers; and
a frame which clamps said insulating layers along a perimeter region thereof against said heating element and which cooperates with said at least one of said insulating layers to form a compartment surrounding said electrically extended terminals, said frame comprising:
first and second sections, said first section further comprising a peripheral wall member and a flange extending inwardly therefrom for engagement with the periphery of one of said insulating layers; and
said second section includes an outer peripheral wall member adapted for mating engagement with said first section peripheral wall member and an inner peripheral wall member, said inner peripheral wall member adapted to engage one of said insulating layers whereby said insulating layers and intermediate heating element are pressed together when said first and second sections are joined together, said inner peripheral wall member having at least one side spaced apart from an associated side of said outer wall member to form said compartment.

8. The apparatus of claim 7 wherein said apparatus further comprises:

a thermostat disposed within said compartment and coupled between one of said terminals and a terminal of an associated insulated power source lead passing through said frame.

9. The apparatus of claim 8 wherein said thermostat is a bimetallic element.

10. The apparatus of claim 8 wherein said compartment also surrounds said thermostat and said lead terminal.

11. The apparatus of claim 8 wherein said apparatus further comprises a rectifier circuit disposed on an opposite side of one of said insulating layers from said heater element and coupled in parallel with said thermostat between said heater element terminal and said terminal of said associated lead.

12. The apparatus of claim 11 wherein said compartment surrounding said heater element terminal also surrounds said thermostat, rectifier circuit and associated lead terminal.

13. The apparatus of claim 11 wherein said apparatus further comprises a fuse coupled between a second heater element terminal and a terminal of an associated lead.

14. The apparatus of claim 13 wherein said heater element terminal and associated lead terminal pairs and associated circuitry coupled therebetween are surrounded by said compartment.

15. The apparatus of claim 7 wherein said heating element comprises a rope element.

16. The apparatus of claim 7 wherein a pair of opposite sides of said inner peripheral wall member are spaced apart from associated sides of said outer peripheral wall member to form a pair of compartments.

17. The apparatus of claim 16 wherein said apparatus further comprises:
   a thermostat disposed within a first one of said compartments and coupled between one of said heater element terminals and a terminal of an associated insulated power source lead passing through said frame;
   a rectifier circuit disposed within said first compartment and coupled in parallel with said thermostat between said one of said terminals and said terminal of said associated insulated power source; and
   a fuse disposed wihin said remaining compartment and coupled between a second heater element terminal and a second terminal of an associated lead.

18. The apparatus of claim 7 wherein the flange of said first section and the inner peripheral wall of said second section define center planar areas of said insulating layers which are open to the surrounding atmosphere.

* * * * *